(12) United States Patent
Luo et al.

(10) Patent No.: US 6,673,363 B2
(45) Date of Patent: *Jan. 6, 2004

(54) TRANSDERMAL AND TOPICAL ADMINISTRATION OF LOCAL ANESTHETIC AGENTS USING BASIC ENHANCERS

(75) Inventors: Eric C. Luo, Plano, TX (US); Nicole T. Gricenko, San Diego, CA (US); Tsung-Min Hsu, San Diego, CA (US)

(73) Assignee: Dermatrends, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/176,265

(22) Filed: Jun. 19, 2002

(65) Prior Publication Data

US 2002/0197284 A1 Dec. 26, 2002

Related U.S. Application Data

(63) Continuation-in-part of application No. 09/972,008, filed on Oct. 4, 2001, which is a continuation-in-part of application No. 09/738,410, filed on Dec. 14, 2001, and a continuation-in-part of application No. 09/738,395, filed on Dec. 14, 2000, which is a continuation-in-part of application No. 09/607,892, filed on Jun. 30, 2000, now abandoned, which is a continuation-in-part of application No. 09/569,889, filed on May 11, 2000, which is a continuation-in-part of application No. 09/465,098, filed on Dec. 16, 1999.

(51) Int. Cl.[7] .......................... A61F 13/00; A61H 15/00
(52) U.S. Cl. ................. 424/449; 424/443; 424/445; 424/447; 424/448; 514/946; 514/947; 514/944
(58) Field of Search ................. 424/449, 443, 424/445, 447, 448; 514/946, 947, 944

(56) References Cited

U.S. PATENT DOCUMENTS

| | | | |
|---|---|---|---|
| 3,028,429 A | 4/1962 | Wilbert et al. | |
| 4,289,749 A | 9/1981 | Keith et al. | |
| 4,704,282 A | 11/1987 | Campbell et al. | |
| 4,789,547 A | 12/1988 | Song et al. | |
| 4,818,541 A | 4/1989 | Sanderson | |
| 4,837,027 A | 6/1989 | Lee et al. | |
| 4,885,312 A | 12/1989 | Wurtman et al. | |
| 5,019,594 A | 5/1991 | Wurtman et al. | |
| 5,021,457 A | 6/1991 | Akin et al. | |
| 5,071,657 A | 12/1991 | Oloff et al. | |
| 5,096,712 A | 3/1992 | Wurtman | |
| 5,152,997 A | 10/1992 | Ebert et al. | |
| 5,260,073 A | 11/1993 | Phipps | |
| 5,318,960 A | 6/1994 | Toppo | |
| 5,362,497 A | 11/1994 | Yamada et al. | |
| 5,422,118 A | 6/1995 | Brown et al. | |
| 5,432,192 A | 7/1995 | Sawanishi et al. | |
| 5,446,070 A | 8/1995 | Mantelle | |
| 5,460,820 A | 10/1995 | Ebert et al. | |
| 5,462,744 A | 10/1995 | Gupte et al. | |
| 5,462,746 A | 10/1995 | Wolter et al. | |
| 5,474,783 A | 12/1995 | Miranda et al. | |
| 5,498,417 A | 3/1996 | Lhila et al. | |
| 5,500,222 A | 3/1996 | Lee et al. | |
| 5,527,832 A | 6/1996 | Chi et al. | |
| 5,532,278 A | 7/1996 | Aberg et al. | |
| 5,534,496 A | 7/1996 | Lee et al. | |
| 5,562,917 A | 10/1996 | Durif et al. | |
| 5,573,778 A | 11/1996 | Therriault et al. | |
| 5,599,554 A | 2/1997 | Majeti | |
| 5,614,211 A | 3/1997 | Gale et al. | |
| 5,674,895 A | 10/1997 | Guittard et al. | |
| 5,807,568 A | 9/1998 | Cody et al. | |
| 5,817,332 A | 10/1998 | Urtti et al. | |
| 5,830,497 A | 11/1998 | Yamanaka et al. | |
| 5,834,513 A | 11/1998 | Ptchelintsev et al. | |
| 5,847,003 A | 12/1998 | Ptchelintsev et al. | |
| 5,879,690 A | 3/1999 | Perricone | |

(List continued on next page.)

FOREIGN PATENT DOCUMENTS

| | | |
|---|---|---|
| CA | 2006425 | 6/1990 |
| EP | 0276561 | 8/1988 |
| EP | 0316065 | 5/1989 |
| EP | 0374725 | 6/1990 |
| EP | 0709088 | 5/1996 |
| EP | 0842662 | 5/1998 |
| FR | 2692145 | 12/1993 |
| JP | 2180835 | 7/1990 |
| JP | 6092843 | 4/1994 |
| KR | 9507098 | 6/1995 |
| WO | WO 82/00099 | 1/1982 |
| WO | WO 94/21271 | 9/1994 |
| WO | WO 97/47354 | 12/1997 |
| WO | WO 99/49844 | 10/1999 |

OTHER PUBLICATIONS

Andrews et al. (1980), "Nitrosation and Mutagenicity of Some amine Drugs," *Toxicology and Applied Pharmacology* 52:237–244.

Andrews et al. (1984), "Mutagenicity of Amine Drugs and Their Products of Nitrosation," *Mutation Research* 135:105–108.

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

(List continued on next page.)

Primary Examiner—Thurman K. Page
Assistant Examiner—Isis Ghali
(74) Attorney, Agent, or Firm—Reed & Eberle LLP; Shelley P. Eberle; Dianne E. Reed

(57) ABSTRACT

Methods are provided for enhancing the permeability of skin or mucosal tissue to topical or transdermal application of local anesthetic agents. The methods entail the use of a base in order to increase the flux of the agent through a body surface while minimizing the likelihood of skin damage, irritation or sensitization. The permeation enhancer can be an inorganic or organic base. Compositions and transdermal systems are also described.

33 Claims, No Drawings

U.S. PATENT DOCUMENTS

| | | | |
|---|---|---|---|
| 5,939,094 | A | 8/1999 | Durif et al. |
| 5,952,000 | A | 9/1999 | Venkateshwaran et al. |
| 5,962,018 | A | 10/1999 | Curtis et al. |
| 5,976,566 | A | 11/1999 | Samour et al. |
| 5,985,317 | A | 11/1999 | Venkateshwaran et al. |
| 5,985,856 | A | 11/1999 | Stella et al. |
| 5,985,860 | A | 11/1999 | Toppo |
| 5,989,586 | A | 11/1999 | Hsu et al. |
| 5,990,113 | A | 11/1999 | Yamazaki et al. |
| 5,990,179 | A | 11/1999 | Gyory et al. |
| 5,993,851 | A | 11/1999 | Foldvari |
| 6,004,577 | A | 12/1999 | Murdock |
| 6,019,988 | A | 2/2000 | Parab et al. |
| 6,019,997 | A | 2/2000 | Scholz et al. |
| 6,123,961 | A | 9/2000 | Aberg |
| 6,132,760 | A | 10/2000 | Hedenstrom et al. |
| 6,139,866 | A | 10/2000 | Chono et al. |
| 6,174,546 | B1 | 1/2001 | Therriault et al. |
| 6,197,331 | B1 | 3/2001 | Lerner et al. |
| 6,204,268 | B1 | 3/2001 | Scarborough et al. |
| 6,207,184 | B1 | 3/2001 | Ikeda et al. |
| 6,214,374 | B1 | 4/2001 | Schmirler et al. |
| 6,270,793 | B1 | 8/2001 | Van Dyke et al. |

OTHER PUBLICATIONS

Greenwald et al. (1999), "Drug Delivery Systems Employing 1,4– or 1,6–Elimination: Poly(Ethylene Glycol) Prodrugs of Amine–Containing Compounds," *J. Med. Chem.* 42(18):3657–3667.

Hiripi et al. (1994), "Characterization of Tyramine and Octopamine Receptors in the Insect (*Locusta Migratoria Migratorioides*) Brain," *Brain Research* 633: 119–126.

Ito et al. (1991), "Skin Pretreatment and the Use of Transdermal Clonidine," *The American Journal of Medicine* 91(1A):42S–49S.

Matsui et al. (1995), "Structure–Activity Relationships of Alkylamines that Inhibit Rat Liver Hydroxysteroid Sulfotransferase Activities In Vitro," *Biochemical Pharmacology* 49(5):739–741.

Maurer–Spurej et al. (1999), "Factors Influencing Uptake and Retention of Amino–containing Drugs in Large Unilamellar Vesicles Exhibiting Transmembrane pH Gradients," *Biochimica et Biophysica Acta* 1416:1–10.

Scherzinger et al. (1990), "Steady State Pharmacokinetics and Dose–Proportionality of Phenylpropanolamine in Healthy Sybjects," *J. Clin. Pharmacol.* 30(4):372–377.

Sharp et al. (1992), "Inhibition of Human and Rabbit Liver Steroid and Xenobiotic UDP–Glucuronosyltransferases by Tertiary Amine Drugs—Implications for Adverse Drug Reactions," *Xenobiotica* 22(1):13–25.

Tong et al. (1991), "Structural Effects on the Binding of Amine Drugs with Diphenylmethyl Functionality to Cyclodextrins. II. A Molecular Modeling Study," *Pharmaceutical Research* 8(10):1307–1312.

Wang et al. (1998), "Coumarin–Based Prodrugs. Part 3: Structural Effects on the Release Kinetics of Esterase–Sensitive Produgs of Amines," *Bioorganic and Medicinal Chemistry* 6:417–426.

Worland et al. (1981), "Effect of Basic Amine Drugs on the Metabolism of Angiotensin I in Rat Lung Homongenates," *J. Pharm. Pharmacol.* 33:794–795.

TRANSDERMAL AND TOPICAL ADMINISTRATION OF LOCAL ANESTHETIC AGENTS USING BASIC ENHANCERS

CROSS-REFERENCE To RELATED APPLICATIONS

This application is a continuation in part of U.S. Ser. No. 09/972,008 filed on Oct. 4, 2001, which is a continuation in part of U.S. Ser. No. 09/738,410 filed on Dec. 14, 2000, which is a continuation in part of U.S. Ser. No. 09/569,889 filed on May 11, 2000, which is a continuation in part of U.S. Ser. No. 09/465,098 filed on Dec. 16, 1999; and is a continuation in part of U.S. Ser. No. 09/738,395 filed on Dec. 14, 2000, which is a continuation in part of U.S. Ser. No. 09/607,892 filed on Jun. 30, 2000, now abandoned.

FIELD OF THE INVENTION

This invention relates generally to the topical and transdermal administration of local anesthetic agents, and more particularly relates to methods and compositions for enhancing the flux of local anesthetic agents through a body surface utilizing a basic permeation enhancer.

BACKGROUND OF THE INVENTION

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences, e.g., gastrointestinal irritation and the like, are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum, which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

Numerous chemical agents have been studied as a means of increasing the rate at which a drug penetrates through the skin. As will be appreciated by those in the field, chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers or "permeation enhancers," as the compounds are referred to herein, are compounds that are innocuous and serve merely to facilitate diffusion of the drug through the stratum corneum. The permeability of many therapeutic agents with diverse physicochemical characteristics may be enhanced using these chemical enhancement means. However, there are skin irritation and sensitization problems associated with high levels of certain enhancers.

There are many potential uses for topical and transdermal delivery of local anesthetic agents. Such uses include the treatment of burns, contact dermatitis, insect bites, pain, pruritus, skin rash, wounds and other dermal injuries; use as part of or in preparation for a surgical procedure; use as a pretreatment prior to needle injection, such as for subcutaneous injections, venipucture, and in particular for intramuscular or intrajoint injections such as for the administration of corticosteroids and other steroids, and so forth.

Accordingly, there is a need for a method that is highly effective in increasing the rate at which local anesthetic agents permeate the skin, does not result in skin damage, irritation, sensitization, or the like, and can be used to effect transdermal delivery of a wide range of compounds within the class of local anesthetic agents. It has now been discovered that basic permeation enhancers as described herein are highly effective permeation enhancers, and provide all of the aforementioned advantages relative to known permeation enhancers. Furthermore, in contrast to many conventional enhancers, transdermal administration of local anesthetic agents with basic permeation enhancers, employed at the appropriate levels, does not result in systemic toxicity.

SUMMARY OF THE INVENTION

One aspect of the invention pertains to a method for enhancing the flux of a local anesthetic agent through a body surface, comprising: (a) administering the local anesthetic agent to a localized region of a human patient's body surface; and (b) administering a basic permeation enhancer to the localized region, the enhancer comprising a pharmaceutically acceptable base and being present in an amount effective to provide a pH within the range of about 8.0–13.0 at the localized region of the body surface during administration of the agent and to enhance the flux of the agent through the body surface without causing damage thereto. The pharmaceutically acceptable base can be an inorganic or an organic base.

Another aspect of the invention relates to a composition for the enhanced delivery of a local anesthetic agent through a body surface, comprising a formulation of: (a) a therapeutically effective amount of the local anesthetic agent; (b) a pharmaceutically acceptable base in an amount effective to provide a pH within the range of about 8.0–13.0 at the body surface during administration of the agent and to enhance the flux of the agent through the body surface without causing damage thereto; and (c) a pharmaceutically acceptable carrier suitable for topical or transdermal drug administration. In one aspect of the invention the pH is about 8.0–11.5 and in another aspect, the pH is about 8.5–10.5. The formulation is typically aqueous. The pharmaceutically acceptable base can be an inorganic or an organic base.

Yet another aspect of the invention pertains to a system for the enhanced topical or transdermal administration of a local anesthetic agent, comprising: (a) at least one drug reservoir containing the local anesthetic agent and a pharmaceutically acceptable base, in an amount effective to enhance the flux of the local anesthetic agent through the body surface without causing damage thereto; (b) a means for maintaining the system in agent and base transmitting relationship to the body surface and forming a body surface-system interface;

and (c) a backing layer that serves as the outer surface of the device during use, wherein the base is effective to provide a pH within the range of about 8.0–13.0 at the body surface-system interface during administration of the local anesthetic agent. In one aspect of the invention the pH is about 8.0–11.5 and in another aspect, the pH is about 8.5–10.5. The pharmaceutically acceptable base can be an inorganic or an organic base.

DETAILED DESCRIPTION OF THE INVENTION

The present invention provides a method for enhancing the flux of local anesthetic agents through a body surface. A local anesthetic agent and a basic permeation enhancer are administered to a localized region of a human patient's body surface. The permeation enhancer is a pharmaceutically acceptable base and is present in an amount effective to: a) provide a pH within the range of about 8.0–13.0 at the localized region of the body surface during administration of the drug and b) enhance the flux of the local anesthetic agent through the body surface without causing damage thereto. Examples of suitable permeation enhancers are described below. The local anesthetic agent and the permeation enhancer may be present in a single pharmaceutical formulation, or they may be in separate pharmaceutical formulations.

The steps of (a) administering the local anesthetic agent and (b) administering the basic permeation enhancer can be done in any order. For example, step (a) can be done prior to step (b); step (b) can be done prior to step (a); and steps (a) and (b) can be done simultaneously. Certain methods may be preferred depending upon the selection of the local anesthetic agent and basic permeation enhancer, as well as taking into consideration ease of patient compliance and so forth. For example, performing steps (a) and (b) simultaneously, is one preferred method of the invention.

I. Definitions And Nomenclature

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a base" includes mixtures of two or more bases, and the like.

In describing and claiming the present invention, the following terminology will be used in accordance with the definitions set out below.

"Active agent," "pharmacologically active agent" and "drug" are used interchangeably herein to refer to local anesthetic agents. The terms also encompass pharmaceutically acceptable, pharmacologically active derivatives and analogs of local anesthetic agents, including, but not limited to, salts, esters, amides, prodrugs, active metabolites, inclusion complexes, analogs, and the like. Therefore, when the terms "active agent," "pharmacologically active agent", "drug" or "local anesthetic agent" are used, it is to be understood that applicants intend to include the active local anesthetic agent per se as well as pharmaceutically acceptable, pharmacologically active salts, esters, amides, prodrugs, active metabolites, inclusion complexes, analogs, etc., which are collectively referred to herein as "pharmaceutically acceptable derivatives".

The term "aqueous" refers to a composition, formulation or drug delivery system that contains water or that becomes water-containing following application to the skin or mucosal tissue.

The term "base" is used in its traditional sense, i.e., a substance that dissolves in water to produce hydroxide ions. The water is typically an aqueous fluid, and may be natural moisture at the skin surface, or the patch or composition that is used may contain added water, and/or be used in connection with an occlusive backing. Similarly, any liquid or semisolid formulation that is used is preferably aqueous or used in conjunction with an overlayer of an occlusive material. Any base may be used provided that the compound provides free hydroxide ions in the presence of an aqueous fluid. Bases can provide free hydroxide ions either directly or indirectly and thus can also be referred to as "hydroxide-releasing agents". Hydroxide-releasing agents that provide free hydroxide ions directly, typically contain hydroxide groups and release the hydroxide ions directly into solution, for example, alkali metal hydroxides. Hydroxide-releasing agents that provide free hydroxide ions indirectly, are typically those compounds that are acted upon chemically in an aqueous environment and the reaction produces hydroxide ions, for example metal carbonates or amines.

"Body surface" is used to refer to skin or mucosal tissue.

"Carriers" or "vehicles" as used herein refer to carrier materials suitable for transdermal or topical drug administration. Carriers and vehicles useful herein include any such materials known in the art, which are nontoxic and do not interact with other components of the composition in a deleterious manner.

"Effective amount" or "a therapeutically effective amount" of a local anesthetic agent is intended to mean a nontoxic but sufficient amount of the local anesthetic agent to provide the desired therapeutic effect. The amount that is effective will vary from subject to subject, depending on the age and general condition of the individual, the particular local anesthetic agent being administered, and the like. Thus, it is not always possible to specify an exact effective amount. However, an appropriate effective amount in any individual case may be determined by one of ordinary skill in the art using routine experimentation. Furthermore, the exact "effective" amount of the local anesthetic agent incorporated into a composition or dosage form of the invention is not critical, so long as the concentration is within a range sufficient to permit ready application of the formulation so as to deliver an amount of the agent that is within a therapeutically effective range.

"Effective amount" or "an effective permeation enhancing amount" of a permeation enhancer refers to a nontoxic, non-damaging but sufficient amount of the enhancer composition to provide the desired increase in skin permeability and, correspondingly, the desired depth of penetration, rate of administration, and amount of local anesthetic agent delivered.

"Penetration enhancement" or "permeation enhancement" as used herein relates to an increase in the permeability of the skin or mucosal tissue to the local anesthetic agent, i.e., so that the rate at which the agent permeates therethrough (i.e., the "flux" of agent through the body surface) is increased relative to the rate that would be obtained in the absence of the permeation enhancer. The enhanced permeation effected through the use of such enhancers can be observed by measuring the rate of diffusion of drug through animal or human skin using, for example a Franz diffusion apparatus as known in the art and as employed in the Examples herein.

"Predetermined area" of skin or mucosal tissue, refers to the area of skin or mucosal tissue through which a drug-enhancer formulation is delivered, and is a defined area of intact unbroken living skin or mucosal tissue. That area will usually be in the range of about 5–200 cm$^2$, more usually in the range of about 5–100 cm$^2$, preferably in the range of about 20–60 cm$^2$. However, it will be appreciated by those skilled in the art of drug delivery that the area of skin or mucosal tissue through which drug is administered may vary significantly, depending on patch configuration, dose, and the like.

"Topical administration" is used in its conventional sense to mean delivery of a local anesthetic agent to the skin or mucosa, as in, for example, the treatment of various skin disorders. Topical administration, in contrast to transdermal administration, provides a local rather than a systemic effect. However, unless otherwise stated or implied, the terms "topical drug administration" and "transdermal drug administration" are used interchangeably.

"Transdermal" drug delivery is meant administration of a local anesthetic agent to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

"Treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

II. The Permeation Enhancers

The permeation enhancer of the invention is an inorganic or an organic pharmaceutically acceptable base. Preferred inorganic bases include inorganic hydroxides, inorganic oxides, inorganic salts of weak acids, and combinations thereof. Preferred organic bases are nitrogenous bases.

It has long been thought that strong bases, such as NaOH, were not suitable as permeation enhancers because they would damage skin. It has been now been discovered that the skin permeability of local anesthetic agents can be enhanced without skin damage by exposing the skin to a base or basic solution, in a skin contacting formulation or patch. The desired pH of the solution on the skin can be obtained using a variety of bases or base concentrations. Accordingly, the pH is selected so as to be low enough so as to not cause skin damage, but high enough to enhance skin permeation to various local anesthetic agents. As such, it is important that the amount of base in any patch or formulation is optimized so as to increase the flux of the agent through the body surface while minimizing any possibility of skin damage. In general, this means that the pH at the body surface in contact with a formulation or drug delivery system of the invention (i.e., the interface between the body surface and the formulation or delivery system) is preferably in the range of approximately 8.0–13.0, preferably about 8.0–11.5, more preferably about 8.5 to 11.5 and most preferably about 8.5–10.5.

In one preferred embodiment, the pH at the interface is the primary design consideration, i.e., the composition or system is designed so as to provide the desired pH at the interface. Anhydrous formulations and transdermal systems may not have a measurable pH, and the formulation or system can be designed so as to provide a target pH at the interface. Moisture from the body surface can migrate into the formulation or system, dissolve the base and thus release the base into solution, which will then provide the desired target pH at the interface. In those instances, a hydrophilic composition is preferred. In addition, when using aqueous formulations, the pH of the formulation may change over time after it is applied on the skin. For example, gels, solutions, ointments, etc., may experience a net loss of moisture after being applied to the body surface, i.e., the amount of water lost is greater than the amount of water received from the body surface. In that case, the pH of the formulation may be different than its pH when manufactured. This problem can be easily remedied by designing the aqueous formulations to provide a target pH at the interface.

In other embodiments of the invention, the pH of the formulation or the drug composition contained within a delivery system will be in the range of approximately 8.0–13.0, preferably about 8.0–11.5, more preferably about 8.5 to 11.5, and most preferably about 8.5–10.5. In one embodiment of the invention the pH of the formulation is higher than the pH at the interface. For example, if an aqueous formulation is used, moisture from the body surface can dilute the formulation, and thus provide for a different pH at the interface, which will typically be lower than that of the formulation itself.

In one preferred embodiment, the body surface is exposed to a base or basic solution for a sufficient period of time so as to provide a high pH at the skin surface, thus creating channels in the skin or mucosa for the drug to go through. It is expected that drug flux is proportional to the strength of the solution and the duration of exposure. However, it is desirable to balance the maximization of drug flux with the minimization of skin damage. This can be done in numerous ways. For example, the skin damage may be minimized by selecting a lower pH within the 8.0–13.0 range, by exposing the skin to the formulation or system for a shorter period of time, or by including at least one irritation-mitigating additive. Alternatively, the patient can be advised to change the location of application with each subsequent administration.

The methods and compositions of the invention are expected to provide an enhanced flux of local anesthetic agents in the range of at least about 1.5-fold, preferably at least about 3-fold, as compared to the flux observed in the absence of the basic enhancers described herein.

While certain preferred amounts are set forth below, it is understood that, for all of the inorganic and organic bases described herein, the optimum amount of any such base will depend on the strength or weakness of the base and its molecular weight, and other factors such as the number of ionizable sites in the active agent being administered and whether there are any acidic species present in the formulation or patch. One skilled in the art may readily determine the optimum amount for any particular base such that the degree of enhancement is optimized while the possibility of damage to the body surface is eliminated or at least substantially minimized.

A. Inorganic Base

Exemplary inorganic bases are inorganic hydroxides, inorganic oxides, inorganic salts of weak acids, and combinations thereof. Preferred inorganic bases are those whose aqueous solutions have a high pH, and are acceptable as food or pharmaceutical additives. Examples of such preferred inorganic bases are those listed below, along with their respective pHs. Some of the bases are identified by their hydrate forms, and it is understood that when referring to a "base", both the hydrated and non-hydrated forms are intended to be included.

| Inorganic base | pH of Aqueous Solution (concentration) |
|---|---|
| Ammonium hydroxide[1, 2, 3] | 11.27 (1 N), 10.27 (0.001 N) |
| Sodium hydroxide[1, 2, 3] | 14 (5%), 13 (0.5%), 12 (0.05%) |
| Potassium hydroxide[1, 2, 3] | 13.5 (0.1 M) |
| Calcium hydroxide[1, 3] | 12.4 (saturated solution in water) |
| Magnesium hydroxide[1, 3] | 9.5 to 10.5 slurry |
| Magnesium oxide[1, 2, 3] | 10.3 (saturated aqueous solution) |
| Calcium oxide[3] | Soluble in water, Form Ca(OH)$_2$ |
| Sodium acetate[1, 3] | ~8.9 (0.1 N) |
| Sodium acetate, trihydrate[1, 2] | 8.9 (0.1 N) |
| Sodium acetate, anhydrous[1, 2] | ~8.9 (0.1 N) |
| Sodium borate decahydrate[1, 2] | ~8.8–9.4, 9.15 to 9.2 (0.01 M) |
| Sodium borate[1, 2, 3] | 8.8–9.4, 9.15 to 9.2 (0.01 M) |
| Sodium metaborate | Strongly alkaline |
| Sodium carbonate[1, 2, 3] | ~11.6 |
| Sodium carbonate hydrate[1] | ~11.6 |
| Sodium carbonate anhydrous | ~11.6 |
| Sodium bicarbonate[1, 2, 3] | 8.3 (0.1 M fresh) |
| Sodium phosphate, tribasic[1, 3] | ~11.5 (0.1%), ~11.7 (0.5%), ~11.9 (1.0%) |
| Sodium phosphate, tribasic dodecahydrate | 11.5 (0.1%), 11.7 (0.5%), 11.9 (1.0%) |
| Sodium phosphate, dibasic, anhydrous[1, 2] | 9.1 (1%) |
| Sodium phosphate, dibasic, heptahydrate[1, 2] | ~9.5 |
| Sodium phosphate, dibasic[1, 3] | ~9.5 |
| Sodium phosphate, dibasic, dihydrate[1] | ~9.5 |
| Sodium phosphate, dibasic, dodecahydrate | ~9.5 |
| Potassium carbonate[1, 3] | ~11.6 |
| Potassium bicarbonate[3] | 8.2 (0.1 M) |
| Potassium citrate[1, 2, 3] | ~8.5 |
| Potassium citrate monohydrate | ~8.5 |
| Potassium acetate[1, 3] | 9.7 (0.1 M) |
| Potassium phosphate, dibasic[1, 2] | Aqueous solution is slightly alkaline |
| Potassium phosphate, tribasic[3] | Aqueous solution is strongly alkaline |
| Ammonium phosphate, dibasic[1, 2, 3] | ~8 |

[1]listed in the "Chemicals in Compliance with Pharmaceutical Standards: Inactive Ingredient Guide"
[2]listed in the "Handbook of Pharmaceutical Additives"
[3]listed in the FDA's food additive database

Inorganic Hydroxides

Inorganic hydroxides include, for example, ammonium hydroxide, alkali metal hydroxide and alkaline earth metal hydroxides, and mixtures thereof. Preferred inorganic hydroxides include ammonium hydroxide; monovalent alkali metal hydroxides such as sodium hydroxide and potassium hydroxide; divalent alkali earth metal hydroxides such as calcium hydroxide and magnesium hydroxide; and combinations thereof.

The amount of inorganic hydroxide included in the compositions and systems of the invention, will typically represent about 0.5–4.0 wt %, preferably about 0.5–3.0 wt %, more preferably about 0.75–2.0 wt %, of a topically applied formulation or of a drug reservoir of a drug delivery system, or patch.

The aforementioned amounts are particularly applicable to those formulations and patches in which the local anesthetic agent is (1) an uncharged molecule, e.g., wherein a basic drug is in nonionized, free-base form, (2) a basic salt of an acidic drug, or (3) there are no additional species in the formulation or patch that could react with or be neutralized by the inorganic hydroxide, to any significant degree.

For formulations and patches in which the agent is in the form of an acid addition salt, and/or wherein there are additional species in the formulations or systems that can be neutralized by or react with the inorganic base (i.e., acidic inactive ingredients), the amount of inorganic hydroxide is preferably the total of (1) the amount necessary to neutralize the acid addition salt and/or other base-neutralizable species (i.e., the "acidic species"), plus (2) about 0.5–4.0 wt %, preferably about 0.5–3.0 wt %, more preferably about 0.75–2.0 wt %, of the formulation or drug reservoir. That is, for an acid addition salt, the enhancer is preferably present in an amount just sufficient to neutralize the salt, plus an additional amount (i.e., about 0.5–4.0 wt %, preferably about 0.5–3.0 wt %, more preferably about 0.75–2.0 wt %) to enhance the flux of the drug through the skin or mucosal tissue. Basic drugs in the form of a neutral, free base or basic salt of acidic drug are usually not affected by a base, and thus for these drugs, the amount in (1) is usually the amount necessary to neutralize inactive components that are acidic. For patches, the aforementioned percentages are given relative to the total weight of the formulation components and the adhesive, gel or liquid reservoir.

Still greater amounts of inorganic hydroxide may be used by controlling the rate and/or quantity of release of the base, preferably during the drug delivery period itself.

Inorganic Oxides

Inorganic oxides include, for example, magnesium oxide, calcium oxide, and the like.

The amount of inorganic oxide included in the compositions and systems of the invention may be substantially higher than the numbers set forth above for the inorganic hydroxide, and may be as high as 20 wt %, in some cases as high as 25 wt % or higher, but will generally be in the range of about 2–20 wt %. These amounts may be adjusted to take into consideration the presence of any base-neutralizable species.

Inorganic Salts of Weak Acids

Inorganic salts of weak acids include, ammonium phosphate (dibasic); alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic); alkaline earth metal salts of weak acids such as magnesium phosphate and calcium phosphate; and the like, and combinations thereof.

Preferred inorganic salts of weak acids include, ammonium phosphate (dibasic) and alkali metal salts of weak acids.

The amount of inorganic salts of weak acids included in the compositions and systems of the invention may be substantially higher than the numbers set forth above for the inorganic hydroxide, and may be as high as 20 wt %, in some cases as high as 25 wt % or higher, but will generally be in the range of approximately 2–20 wt %. These amounts may be adjusted to take into consideration the presence of any base-neutralizable species.

B. Organic Bases

Organic bases suitable for use in the invention are compounds having an amino group, amido group, an oxime, a cyano group, an aromatic or non-aromatic nitrogen-containing heterocycle, a urea group, and combinations thereof. More specifically, examples of suitable organic bases are nitrogenous bases, which include, but are not limited to, primary amines, secondary amines, tertiary amines, amides, oximes, cyano (—CN) containing groups, aromatic and non-aromatic nitrogen-containing heterocycles, urea, and mixtures thereof. Preferred organic bases are primary amines, secondary amines, tertiary amines, aromatic and non-aromatic nitrogen-containing heterocycles, and mixtures thereof.

For nitrogenous bases, the amount of enhancing agent will typically represent about 0.5–4.0 wt %, preferably about 0.5–3.0 wt %, more preferably about 0.75–2.0 wt %, of a topically applied formulation or of a drug reservoir of a drug delivery system or a patch. These amounts may be adjusted to take into consideration the presence of any base-neutralizable species.

Still greater amounts of the nitrogenous base may be used depending on the strength of the base and the rate and/or quantity of release of the nitrogenous base preferably during the drug delivery period itself.

Preferred organic bases are those whose aqueous solutions have a high pH or a high pKa (more preferably a pKa>9), and are acceptable as food or pharmaceutical additives. Examples of such preferred organic bases are those listed below, along with their respective pHs (or pKa values).

| Organic base | pH of Aqueous Solution (concentration) |
| --- | --- |
| 2-amino-2-methyl-1,3-propanediol[1] | 10.8 (0.1 m) |
| 2-amino-2-methyl-1-propanol[1] | 11.3 (0.1 m) |
| Diethanolamine[1] | 11.0 (0.1 N) |
| Triethanolamine[1] | 10.5 (0.1 N) |
| Butylamine[2] | pKa = 10.56 |
| Dimethylamine[2] | Strong base, pKa = 10.73 |
| Cyclohexylamine[2] | Strong base, pKa = 10.64 |
| Ethylenediamine[2] | Strong base, pKa = 10.71 |
| Isopentylamine[2] | pKa = 10.6 |
| Monoethanolamine[2] | 12.1 (25%), 12.05 (0.1 N), pKa = 9.4 |
| Phenethylamine[2] | Strong base, pKa = 9.83 |
| Piperidine[2] | Strong base, pKa = 11.12 |
| Pyrrolidine[2] | Strong base, pKa = 11.27 |
| Trimethylamine[2] | Strong base, pKa = 9.81 |

[1]listed in the "Handbook of Pharmaceutical Additives"
[2]listed in the FDA's food additive database Amines Amines are compounds that include at least one primary amino (—$NH_2$) group, mono-substituted (secondary) amino group or di-substituted (tertiary) amino group.

Primary amino groups, secondary amino groups, and tertiary amino groups may be generically grouped as encompassed by the molecular structure —$NR^1R^2R^3$ wherein $R^1$, $R^2$, and $R^3$ may be the same or different and are generally selected from the group consisting of H, alkyl, hydroxyalkyl, alkoxyalkyl, alkenyl, hydroxyalkenyl, alkoxyalkenyl, cycloalkyl, cycloalkyl-substituted alkyl, monocyclic aryl, and monocyclic aryl-substituted alkyl, all of which may be substituted with one or more nonhydrocarbyl substituents, e.g., 1 to 3 halo, hydroxyl, thiol, or lower alkoxy groups.

Exemplary primary amines include 2-aminoethanol, 2-aminoheptane, 2-amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, methylamine, α-methylbenzylamine, phenethylamine, propylamine, and tris(hydroxymethyl)aminomethane.

Exemplary secondary amines include compounds that contain groups such as methylamino, ethylamino, isopropylamino, butylamino, cyclopropylamino, cyclohexylamino, n-hexylamino, phenylamino, benzylamino, chloroethylamino, hydroxyethylamino, and so forth. Exemplary secondary amines include diethanolamine, diethylamine, diisopropylamine, and dimethylamine.

Exemplary tertiary amines include compounds that contain groups such as dibutylamino, diethylamino, dimethylamino, diisopropylamino, ethylchloroethylamino, ethylcyclopropylamino, methylhexylamino, methylcyclohexylamino, methylpropylamino, methylbenzylamino, methyl-p-chlorophenylamino, methylcyclohexylamino, methylphenylamino, methyltoluylamino, and so forth. Exemplary tertiary amines include N,N-diethylaniline, N,N-dimethylglycine, triethanolamine, triethylamine, and trimethylamine.

Amides

Amides are compounds that include an amido group that has the molecular structure —(CO)—$NR^1R^2$ where $R^1$ and $R^2$ can be the same or different, and are generally selected from the groups consisting of H, alkyl, hydroxyalkyl, alkoxyalkyl, alkenyl, hydroxyalkenyl, alkoxyalkenyl, cycloalkyl, cycloalkyl-substituted alkyl, monocyclic aryl, and monocyclic aryl-substituted alkyl, all of which may be substituted with one or more nonhydrocarbyl substituents, e.g., 1 to 3 halo, hydroxyl, thiol, or lower alkoxy groups.

Aromatic Nitrogen-Containing Heterocycles

Aromatic nitrogen-containing heterocycles, typically contain a 5- or 6-membered monocyclic substituent, or a bicyclic fused or linked 5- or 6-membered ring, such as imidazolyl, indolyl, pyridinyl, pyrimidinyl, pyrrolyl, quinolinyl, tetrazolyl, 1,2,4-triazolyl, etc.

Aromatic nitrogen-containing heterocycles suitable as the organic base herein include, by way of example, 2-aminopyridine, benzimidazole, 2,5-diaminopyridine, 2,4-dimethylimidazole, 2,3-dimethylpyridine, 2,4-dimethylpyridine, 3,5-dimethylpyridine, imidazole, methoxypyridine, γ-picoline, 2,4,6-trimethylpyridine, and combinations thereof.

Non-Aromatic Nitrogen-Containing Heterocycles

Non-aromatic nitrogen-containing heterocycles, typically contain 4- to 6-membered rings such as acetimido, morpholinyl, lactams and imides (e.g., γ-butyrolactam, ε-caprolactam, N-phenyl-β-propiolactam), phthalimido, piperidyl, piperidino, piperazinyl, pyrrolidinyl, succinimido, etc.

Non-aromatic nitrogen-containing heterocycles include, by way of example, 1,2-dimethylpiperidine, 2,5- dimethylpiperazine, 1,2-dimethylpyrrolidine, 1-ethylpiperidine, n-methylpyrrolidine, morpholine, piperazine, piperidine, pyrrolidine, 2,2,6,6-tetramethylpiperidine, 2,2,4-trimethylpiperidine, and combinations thereof.

III. The Active Agent

The active agent administered may be any local anesthetic agent that is suitable for topical, transdermal or transmucosal delivery (e.g., can be delivered through body surfaces and membranes, including skin) and induces the desired local or systemic effect. Exemplary uses for such agents include, by way of example and not limitation, treatment for burns, contact dermatitis, insect bites, pain, pruritus, skin rash, wounds, and so forth.

Exemplary local anesthetics that may be administered using the methods, compositions and systems of the invention include, but are not limited to, alcohols such as phenol; benzyl benzoate; calamine; chloroxylenol; dyclonine; ketamine; menthol; pramoxine; resorcinol; troclosan; and procaine drugs such as benzocaine, bupivacaine, chloroprocaine, cinchocaine, cocaine, dexivacaine, diamocaine, dibucaine, etidocaine, hexylcaine, levobupivacaine, lidocaine, mepivacaine, oxethazaine, prilocaine, procaine, proparacaine, propoxycaine, pyrrocaine, risocaine, rodocaine, ropivacaine, and tetracaine; and pharmaceutically acceptable derivatives thereof, and combinations thereof.

Derivatives of these compounds, such as pharmaceutically acceptable salts and esters are also of particular interest, for example, bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, tetracaine HCl, and so forth, and so forth.

Preferred local anesthetics include bupivacaine, chloroprocaine, dibucaine, etidocaine, levobupivacaine, lidocaine, mepivacaine, prilocaine, ropivacaine, tetracaine, and pharmaceutically acceptable salts and esters thereof.

The local anesthetic agent may be administered, if desired, in the form of a salt, ester, amide, prodrug, derivative, or the like, provided the salt, ester, amide, prodrug or derivative is suitable pharmacologically. Salts, esters, amides, prodrugs and other derivatives of local anesthetic agents may be prepared using standard procedures known to those skilled in the art of synthetic organic chemistry and described, for example, by *March's Advanced Organic Chemistry: Reactions, Mechanisms and Structure,* 5th Ed. (Wiley-Interscience, 2001).

For example, acid addition salts are prepared from the free base (e.g., an amine drug) using conventional methodology, by reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids.

Preparation of basic salts of acids are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

For those local anesthetic agents that may be chiral in nature and can thus be in an enantiomerically pure form or in a racemic mixture, the drug may be incorporated into the present dosage units either as the racemate or in the enantiomerically pure form.

The amount of local anesthetic agent administered will depend on a number of factors and will vary from subject to subject and depend on the particular agent administered, the particular disorder or condition being treated, the severity of the symptoms, the subject's age, weight and general condition, and the judgment of the prescribing physician. In particular, due to differences in systemic absorption and toxicity, the concentration of the drug used depends on the condition being treated or the anesthetic procedure the patient may be undergoing.

Other factors, specific to transdermal drug delivery, include the solubility and permeability of the carrier and adhesive layer in a drug delivery device, if one is used, and the period of time for which such a device will be fixed to the skin or other body surface. The minimum amount of local anesthetic agent is determined by the requirement that sufficient quantities of drug must be present in a device or composition to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

IV. Pharmaceutical Formulations

One embodiment of the invention is a composition for the enhanced delivery of a local anesthetic agent through a body surface, comprising a formulation of: (a) a therapeutically effective amount of the drug; (b) a pharmaceutically acceptable inorganic or organic base in an amount effective to provide a pH within the range of about 8.0–13.0 at the localized region of the body surface during administration of the agent and to enhance the flux of the agent through the body surface without causing damage thereto; and (c) a pharmaceutically acceptable carrier suitable for topical or transdermal drug administration. The formulation is typically, but not necessarily, an aqueous formulation. The pH is more preferably about 8.0–11.5, and most preferably about 8.5–10.5.

Accordingly, while the method of delivery of the active agent may vary, the method will typically involve application of a formulation or drug delivery system containing a pharmaceutically acceptable inorganic or organic base to a predetermined area of the skin or other tissue for a period of time sufficient to provide the desired local or systemic effect. The method may involve direct application of the composition as an ointment, gel, cream, or the like, or may involve use of a drug delivery device. In either case, water is preferably present in order for the hydroxide ions to be provided by the base, and thus enhance the flux of the active agent through the patient's body surface. Thus, such a formulation or drug reservoir may be aqueous, i.e., contain water, or may be nonaqueous and used in combination with an occlusive backing so that moisture evaporating from the body surface is maintained within the formulation or transdermal system during drug administration. In some cases, however, e.g., with an occlusive gel, a nonaqueous formulation may be used with or without an occlusive backing layer.

Suitable formulations include ointments, creams, gels, lotions, solutions, pastes, and the like. Ointments, as is well known in the art of pharmaceutical formulation, are semisolid preparations that are typically based on petrolatum or other petroleum derivatives. The specific ointment foundation to be used, as will be appreciated by those skilled in the art, is one that will provide for optimum drug delivery, and, preferably, will provide for other desired characteristics as well, e.g., emolliency or the like. As with other carriers or vehicles, an ointment foundation should be inert, stable, nonirritating and nonsensitizing. As explained in Remington: The Science and Practice of Pharmacy, 20$^{th}$ edition (Lippincott Williams & Wilkins, 2000), ointment foundations may be grouped in four classes: oleaginous, emulsifiable, emulsion, and water-soluble. Oleaginous ointment foundations include, for example, vegetable oils, fats obtained from animals, and semisolid hydrocarbons obtained from petroleum. Emulsifiable ointment foundations, also known as absorbent ointment foundations, contain little or no water and include, for example, hydroxystearin sulfate, anhydrous lanolin and hydrophilic petrolatum. Emulsion ointment foundations are either water-in-oil (W/O) emulsions or oil-in-water (O/W) emulsions, and include, for example, cetyl alcohol, glyceryl monostearate, lanolin and stearic acid. Preferred water-soluble ointment foundations are prepared from polyethylene glycols of varying molecular weight.

Creams, as also well known in the art, are viscous liquids or semisolid emulsions, either oil-in-water or water-in-oil. Cream foundations are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solute) in another liquid such that the molecules of the dissolved substance are dispersed among those of the solvent. The solution may contain other pharmaceutically acceptable chemicals to buffer, stabilize or preserve the solute. Commonly used examples of solvents used in preparing solutions are ethanol, water, propylene glycol or any other pharmaceutically acceptable vehicle.

Pastes are semisolid dosage forms in which the active agent is suspended in a suitable foundation. Depending on the nature of the foundation, pastes are divided between fatty pastes or those made from single-phase, aqueous gels. The foundation in a fatty paste is generally petrolatum or hydrophilic petrolatum or the like. The pastes made from single-phase aqueous gels generally incorporate carboxymethyl-cellulose or the like as the foundation.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N-[1-2,3-dioleyloxy)propyl]-N,N,N-triethylammonium liposomes are available under the tradename Lipofectin® (GIBCO BRL, Grand Island, N.Y.). Anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline, dioleoylphosphatidyl glycerol, dioleoylphoshatidyl ethanolamine, among others. These materials can also be mixed with N-[1-2,3-dioleyloxy)propyl]-N,N,N-triethylammonium (DOTMA) in appropriate ratios. Methods for making liposomes using these materials are well known in the art.

Micelles are known in the art and are comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally, although not necessarily, formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those local anesthetic agents having an unusually low rate of permeation through the skin or mucosal tissue, it may be desirable to include a second permeation enhancer in the formulation in addition to the inorganic or organic base enhancer, although in a preferred embodiment the base enhancer is administered without any other permeation enhancers. Any other enhancers should, like the base enhancer, minimize the possibility of skin damage, irritation, and systemic toxicity. Examples of classes of suitable secondary enhancers (or "co-enhancers") include, but are not limited to, fatty acids, both saturated and unsaturated; fatty alcohols; bile acids; nonionic surfactants, including esters of fatty acids, fatty (long-chain alkyl or alkenyl) esters of monohydric alcohols, diols, and polyols, diols and polyols that are both esterified with a fatty acid and substituted with a polyoxyalkylene, polyoxyalkylene fatty acid esters, polyoxyalkylene fatty ethers, polyoxyalkylene fatty ethers, and polyglyceryl fatty acid esters; amines; amides; N-alkyl-azacycloalkanones and N-alkyl-azacycloalkenones; hydrocarbon solvents; terpenes; lower alkyl esters; cyclodextrin enhancers; nitrogen-containing heterocycles; sulfoxides; and urea and its derivatives.

Specific examples of suitable co-enhancers include ethers such as diethylene glycol monoethyl ether (available commercially as Transcutol®, Gattefosse SA) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as dimethylsulfoxide and decylmethylsulfoxide may also be used, but are less preferred. *Percutaneous Penetration Enhancers,* eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the local anesthetic agent, the base enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the formulation at a concentration effective to mitigate irritation or skin damage, typically representing not more than about 20 wt %, more typically not more than about 5 wt %, of the formulation.

The concentration of the local anesthetic agent in the formulation will typically depend upon a variety of factors, including the disease or condition to be treated, the nature and activity of the agent, the desired effect, possible adverse reactions, the ability and speed of the agent to reach its intended target, and other factors within the particular knowledge of the patient and physician. Preferred formulations will typically contain on the order of about 0.5–50 wt %, preferably about 5–30 wt %, active agent.

V. Drug Delivery Systems

An alternative and preferred method involves the use of a drug delivery system, e.g., a topical or transdermal "patch," wherein the local anesthetic agent is contained within a laminated structure that is to be affixed to the skin. In such a structure, the drug composition is contained in a layer, or "reservoir," underlying an upper backing layer that serves as the outer surface of the device during use. The laminated structure may contain a single reservoir, or it may contain multiple reservoirs.

Accordingly, another embodiment of the invention is a system for the enhanced topical or transdermal administration of a local anesthetic agent, comprising: (a) at least one drug reservoir containing the local anesthetic agent and a pharmaceutically acceptable inorganic or organic base in an amount effective to enhance the flux of the local anesthetic agent through the body surface without causing damage thereto; (b) a means for maintaining the system in agent and base transmitting relationship to the body surface and forming a body surface-system interface; and (c) a backing layer that serves as the outer surface of the device during use, wherein the base is effective to provide a pH within the range of about 8.0–13.0 at the body surface-system interface during administration of the drug. The pH is more preferably about 8.0–11.5, and most preferably about 8.5–10.5.

In one embodiment, the drug reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, inorganic or organic base, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing the local anesthetic agent, the base enhancer, or other components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure preferably includes a release liner. Immediately prior to use, this layer is removed from the device so that the system may be affixed to the skin. The release liner should be made from a drug/vehicle impermeable material, and is a disposable element, which serves only to protect the device prior to application. Typically, the release liner is formed from a material impermeable to the local anesthetic agent and the base enhancer, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or pouch, or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a base enhancer, an additional enhancer, or some other component contained in the drug delivery system.

A rate-controlling membrane, if present, will be included in the system on the skin side of one or more of the drug reservoirs. The material used to form such a membrane is selected so as to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5–200 $cm^2$, preferably 5–100 $cm^2$, more preferably 20–60 $cm^2$. That area will vary, of course, with the amount of local anesthetic agent to be delivered and the flux of the agent through the body surface. Larger patches can be used to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, local anesthetic agent and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by soaking in a drug/vehicle mixture. In general, transdermal systems of the invention are fabricated by solvent evaporation, film casting, melt extrusion, thin film lamination, die cutting, or the like. The inorganic or organic base permeation enhancer will generally be incorporated into the device during patch manufacture rather than subsequent to preparation of the device. Thus, for acid addition salts of basic drugs (e.g., hydrochloride salts of amine drugs), the enhancer will neutralize the drug during manufacture of the drug delivery system, resulting in a final drug delivery system in which the drug is present in nonionized, neutral form along with an excess of base to serve as a permeation enhancer. For nonionized acidic drugs, the base will neutralize such drugs by converting them to the ionized drug in salt form.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such an adhesive overlayer, the delivery system will remain in place for the required period of time.

Other types and configurations of transdermal drug delivery systems may also be used in conjunction with the method of the present invention, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the topically applied formulations of the invention, the local anesthetic agent and enhancer composition contained within the drug reservoir(s) of these laminated systems may comprise a number of additional components. In some cases, the drug and enhancer may be delivered neat, i.e., in the absence of additional liquid. In most cases, however, the drug will be dissolved, dispersed or suspended in a suitable pharmaceutically acceptable vehicle, typically a solvent or gel. Other components that may be present include preservatives, stabilizers, surfactants, solubilizers, additional enhancers, and the like.

The invention accordingly provides a novel and highly effective means for increasing the flux of a local anesthetic agent through the body surface (skin or mucosal tissue) of a human or animal. The base enhancers discussed herein, employed in specific amounts relative to a formulation or drug reservoir, may be used as permeation enhancers with a wide variety of local anesthetic agents, including free acids, free bases, acid addition salts of basic drugs, basic addition salts of acidic drugs, nonionizable drugs, peptides and proteins. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation, particularly topical and transdermal drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 10th Ed.(2001).

The following examples are put forth so as to provide those of ordinary skill in the art with a complete disclosure and description of how to practice the methods as well as make and use the compositions of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. The following abbreviations will be used in accordance with the definitions set out below.

EXAMPLES

Abbreviations

| PG | Propylene glycol |
| PIB | Polyisobutylene |

Methods

Preparation of Round Disc Samples

Each formulation was coated onto a release liner and dried in an oven at 65° C. for two hours to remove water and other solvents. The dried drug-in-adhesive/release liner film was laminated to a backing film. The backing/drug-in-adhesive/release liner laminate was then cut into round discs with a diameter of 9/16 inch.

Measurement of Permeation of Drugs Through Human Cadaver Skin

The in vitro permeation of drugs through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution.

Measurement of pH

The pH of the patches was measured using the following procedures. A 2.4 $cm^2$ circular patch was punched out. Ten ml purified water was pipetted into a glass vial, and a stir bar was added. The liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter.

Example 1

An in-vitro skin permeation study was conducted using three lidocaine transdermal systems, designated, Lido-1, Lido-2, Lido-3, the compositions of which are set forth in Table 1. Round disc samples were prepared as described in the Methods section. The theoretical percent weight for each ingredient after drying (calculated assuming all the volatile ingredients were completely removed during drying) is listed in Table 2.

TABLE 1

Component Weight and Weight Percent Based on Total Solution Weight

|  | Lido-1 g (wt %) | Lido-2 g (wt %) | Lido-3 g (wt %) |
| --- | --- | --- | --- |
| Lidocaine | 0.50 (9.1) | 0.50 (8.9) | 0.50 (8.8) |
| PG | 0.50 (9.1) | 0.50 (8.9) | 0.50 (8.8) |

TABLE 1-continued

Component Weight and Weight Percent Based on Total Solution Weight

|  | Lido-1 g (wt %) | Lido-2 g (wt %) | Lido-3 g (wt %) |
|---|---|---|---|
| Water | 0 | 0.07 (1.2) | 0.11 (1.8) |
| PIB adhesive (30% solid) | 4.00 (72.7) | 4.00 (70.9) | 4.00 (70.1) |
| NaOH | 0 | 0.07 (1.2) | 0.11 (1.8) |
| n-Heptane | 0.50 (9.1) | 0.50 (8.9) | 0.50 (8.8) |

TABLE 2

Component Weight and Weight Percent Based on Dried Film Weight

|  | Lido-1 g (wt %) | Lido-2 g (wt %) | Lido-3 g (wt %) |
|---|---|---|---|
| Lidocaine | 0.50 (22.7) | 0.50 (22.0) | 0.50 (21.7) |
| PG | 0.50 (22.7) | 0.50 (22.0) | 0.50 (21.7) |
| PIB adhesive | 1.20 (54.4) | 1.20 (52.9) | 1.20 (52.1) |
| NaOH | 0 | 0.07 (3.1) | 0.11 (4.6) |

Since the reaction between lidocaine and NaOH is not expected to be significant, the concentration of NaOH in the system is assumed to be independent from the amount of lidocaine added. Therefore, the NaOH concentration listed in Table 2 equals the excess NaOH concentration, which can be calculated by the following equation.

$$[NaOH_{excess}]=[NaOH_{total}]-[NaOH_{needed\ for\ neutralization}]$$

The in vitro permeation of lidocaine through human cadaver skin from these discs was measured as described in the Methods section. Three diffusion cells were used for each formulation. The receiver solution, 5% ethanol/95% PBS buffer (0.05 M $KH_2PO_4$ with 0.15 M NaCl, pH adjusted to 6.5), was completely withdrawn and replaced with fresh receiver solution at each time point. The samples taken were analyzed by an HPLC for the concentration of lidocaine in the receiver solution. The cumulative amount of lidocaine across human cadaver skin was calculated using the measured lidocaine concentrations in the receiver solutions.

TABLE 3

Cumulative Amount of Lidocaine ($mg/cm^2$)

| Time | Lido-1 | Lido-2 | Lido-3 |
|---|---|---|---|
| 5 hours | 0.069 | 0.126 | 0.300 |
| 15.5 hours | 0.237 | 0.410 | 0.816 |
| 23.75 hours | 0.428 | 0.632 | 1.169 |

The pH of the patches was measured as described in the Methods section.

TABLE 4

Excess NaOH Concentration (wt %) and pH

|  | Lido-1 | Lido-2 | Lido-3 |
|---|---|---|---|
| Excess NaOH Concentration | 0 | 3.1% | 4.6% |
| pH | 8.86 | 10.44 | 10.87 |

The pH of the lidocaine patch measured increased from 8.86 to 10.87 when the calculated excess NaOH concentration in the dried patch was increased from 0 % to 4.6 %. The cumulative amount of lidocaine across human cadaver skin at 24 hours increased from 0.428 $mg/cm^2$ to 1.169 $mg/cm^2$ when the calculated excess NaOH concentration in the dried patch was increased from 0% to 4.6%.

The formulation of Lido-2 provided up to 1.5-fold more lidocaine flux than in the absence of NaOH (Lido-1). The highest pH formulation evaluated, Lido-3, provided up to 3-fold more flux than in the absence of NaOH.

All patents, publications, and other published documents mentioned or referred to in this specification are herein incorporated by reference in their entirety.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

Accordingly, the scope of the invention should therefore be determined with reference to the appended claims, along with the full range of equivalents to which those claims are entitled.

We claim:

1. A method for enhancing the flux of a local anesthetic agent through a body surface, comprising:
   (a) administering the local anesthetic agent to a localized region of a human patient's body surface; and
   (b) administering a basic permeation enhancer to the localized region, the enhancer comprising a pharmaceutically acceptable inorganic base and being present in an amount effective to provide a pH within the range of about 8.0–13.0 at the localized region of the body surface during administration of the local anesthetic agent and to enhance the flux of the local anesthetic agent through the body surface without causing damage thereto.

2. The method of claim 1 wherein the pH is within the range of about 8.0–11.5.

3. The method of claim 2 wherein the pH is within the range of about 8.5–10.5.

4. The method of claim 1 wherein the base is selected from the group consisting of ammonium hydroxide, sodium hydroxide, potassium hydroxide, calcium hydroxide, magnesium hydroxide, magnesium oxide, calcium oxide, sodium acetate, sodium borate, sodium metaborate, sodium carbonate, sodium bicarbonate, sodium phosphate, potassium carbonate, potassium bicarbonate, potassium citrate, potassium acetate, potassium phosphate, ammonium phosphate, and combinations thereof.

5. The method of claim 1 wherein the base is selected from the group consisting of inorganic hydroxides, inorganic oxides, inorganic salts of weak acids, and combinations thereof.

6. The method of claim 5 wherein the base is an inorganic hydroxide.

7. The method of claim 6 wherein the inorganic hydroxide is selected from the group consisting of ammonium hydroxide, alkali metal hydroxides, and alkaline earth metal hydroxides.

8. The method of claim 7 wherein the inorganic hydroxide is ammonium hydroxide.

9. The method of claim 7 wherein the inorganic hydroxide is an alkali metal hydroxide selected from the group consisting of sodium hydroxide and potassium hydroxide.

10. The method of claim 7 wherein the inorganic hydroxide is an alkaline earth metal hydroxide selected from the group consisting of calcium hydroxide and magnesium hydroxide.

11. The method of claim 5 wherein the base is an inorganic oxide.

12. The method of claim 11 wherein the inorganic oxide is selected from the group consisting of magnesium oxide and calcium oxide.

13. The method of claim 5 wherein the base is an inorganic salt of a weak acid.

14. The method of claim 13 wherein the inorganic salt of a weak acid is selected from the group consisting of ammonium phosphate, alkali metal salts of weak acids, and alkaline earth metal salts of weak acids.

15. The method of claim 14 wherein the inorganic salt of a weak acid is ammonium phosphate.

16. The method of claim 14 wherein the inorganic salt of a weak acid is an alkali metal salt of a weak acid selected from the group consisting of sodium acetate, sodium borate, sodium metaborate, sodium carbonate, sodium bicarbonate, sodium phosphate, potassium carbonate, potassium bicarbonate, potassium citrate, potassium acetate, and potassium phosphate.

17. The method of claim 1 wherein the body surface is skin.

18. The method of claim 1 wherein the body surface is mucosal tissue.

19. The method of claim 1 wherein the local anesthetic agent and basic permeation enhancer are present in a single pharmaceutical formulation.

20. The method of claim 1 wherein the local anesthetic agent and basic permeation enhancer are present in separate pharmaceutical formulations.

21. The method of claim 20 wherein steps (a) and (b) are done simultaneously.

22. The method of claim 20 wherein step (a) is done prior to step (b).

23. The method of claim 20 wherein step (b) is done prior to step (a).

24. The method of claim 1 wherein the local anesthetic agent and basic permeation enhancer are administered by applying a drug delivery device to the localized region of the patient's body surface thereby forming a body surface-delivery device interface, the device comprising the local anesthetic agent and basic permeation enhancer, and having an outer backing layer that serves as the outer surface of the device during use.

25. The method of claim 1 wherein the basic permeation enhancer is contained within an aqueous formulation.

26. The method of claim 25 wherein the aqueous formulation has a pH within the range of about 8.0–13.0.

27. The method of claim 26 wherein the pH is within the range of about 8.0–11.5.

28. The method of claim 27 wherein the pH is within the range of about 8.5–10.5.

29. The method of claim 25 wherein the aqueous formulation is selected from the group consisting of a cream, a gel, a lotion, and a paste.

30. The method of claim 1 wherein the local anesthetic agent is selected from the group consisting of benzocaine, benzyl benzoate, bupivacaine, calamine, chloroprocaine, chloroxylenol, cinchocaine, cocaine, dexivacaine, diamocaine, dibucaine, dyclonine, etidocaine, hexylcaine, ketamine, levobupivacaine, lidocaine, menthol, mepivacaine, oxethazaine, phenol, pramoxine, prilocaine, procaine, proparacaine, propoxycaine, pyrrocaine, resorcinol, risocaine, rodocaine, ropivacaine, tetracaine, troclosan, and pharmaceutically acceptable derivatives thereof, and combinations thereof.

31. The method of claim 30 wherein the local anesthetic agent is selected from the group consisting of bupivacaine, chloroprocaine, dibucaine, etidocaine, levobupivacaine, lidocaine, mepivacaine, prilocaine, ropivacaine, tetracaine, and pharmaceutically acceptable derivatives thereof.

32. The method of claim 1 wherein the flux of the local anesthetic agent is enhanced by at least about 1.5-fold.

33. The method of claim 32 wherein the flux of the local anesthetic agent is enhanced by at least about 3-fold.

* * * * *

UNITED STATES PATENT AND TRADEMARK OFFICE
CERTIFICATE OF CORRECTION

PATENT NO.   : 6,673,363 B2
DATED        : January 6, 2004
INVENTOR(S)  : Eric C. Luo et al.

It is certified that error appears in the above-identified patent and that said Letters Patent is hereby corrected as shown below:

Title page,
Item [63], Related U.S. Application Data, after "application No. 09/738,410, filed on", please delete "December 14, 2001" and insert -- December 14, 2000 --.

Signed and Sealed this

Eighteenth Day of May, 2004

JON W. DUDAS
*Acting Director of the United States Patent and Trademark Office*